(12) United States Patent
Soucaille (10) Patent No.: US 8,236,994 B2
(45) Date of Patent: Aug. 7, 2012

(54) PROCESS FOR THE BIOLOGICAL PRODUCTION OF 1,3-PROPANEDIOL FROM GLYCEROL WITH HIGH YIELD

(75) Inventor: Philippe Soucaille, Deyme (FR)

(73) Assignee: Metabolic Explorer, Saint Beauzire (FR)

( * ) Notice: Subject to any disclaimer, the term of this patent is extended or adjusted under 35 U.S.C. 154(b) by 464 days.

(21) Appl. No.: 12/447,686

(22) PCT Filed: Oct. 31, 2006

(86) PCT No.: PCT/EP2006/067987
§ 371 (c)(1),
(2), (4) Date: Apr. 29, 2009

(87) PCT Pub. No.: WO2008/052595
PCT Pub. Date: May 8, 2008

(65) Prior Publication Data
US 2010/0137655 A1 Jun. 3, 2010

(51) Int. Cl.
C07C 31/20 (2006.01)
C12P 7/18 (2006.01)
C12N 1/20 (2006.01)
(52) U.S. Cl. ............... 568/852; 435/158; 435/252.7
(58) Field of Classification Search ............ 568/852; 435/158, 252.7
See application file for complete search history.

(56) References Cited

U.S. PATENT DOCUMENTS

| | | | |
|---|---|---|---|
| 1,315,585 A | 9/1919 | Weizmann |
| 4,443,542 A | 4/1984 | Hayashida et al. |
| 4,521,516 A | 6/1985 | Lemme et al. |
| 4,539,293 A | 9/1985 | Bergstrom et al. |
| 4,649,112 A | 3/1987 | Datta et al. |
| 4,777,135 A | 10/1988 | Husted et al. |
| 5,063,156 A | 11/1991 | Glassner et al. |
| 5,254,467 A | 10/1993 | Kretschmann et al. |
| 5,599,689 A | 2/1997 | Haynie et al. |
| 5,633,362 A | 5/1997 | Nagarajan et al. |
| 5,686,276 A | 11/1997 | Laffend et al. |
| 5,753,474 A | 5/1998 | Ramey |
| 6,013,494 A | 1/2000 | Nakamura et al. |
| 6,358,717 B1 | 3/2002 | Blaschek et al. |
| 6,406,895 B1 | 6/2002 | Defretin et al. |
| 6,432,686 B1 | 8/2002 | Bulthuis et al. |
| 6,468,773 B1 | 10/2002 | Donald et al. |
| 6,514,733 B1 | 2/2003 | Emptage et al. |
| 6,803,218 B1 | 10/2004 | Seyfried et al. |
| 7,005,291 B1 | 2/2006 | Nair et al. |
| 7,074,608 B1 | 7/2006 | Dunn-Coleman et al. |
| 7,169,588 B2 | 1/2007 | Burch et al. |
| 7,223,567 B2 | 5/2007 | Ka-Yiu et al. |
| 7,232,664 B2 | 6/2007 | Van Hoek et al. |
| 7,267,972 B2 | 9/2007 | Sarcabal et al. |
| 7,371,558 B2 | 5/2008 | Cervin et al. |
| 2004/0152159 A1 | 8/2004 | Causey et al. |
| 2005/0089979 A1 | 4/2005 | Ezeji et al. |
| 2006/0073577 A1 | 4/2006 | Ka-Yiu et al. |
| 2007/0020740 A1 | 1/2007 | Bennett et al. |
| 2007/0087423 A1 | 4/2007 | Murakami et al. |
| 2007/0148749 A1 | 6/2007 | Yasuda et al. |
| 2007/0178569 A1 | 8/2007 | Leschine et al. |
| 2007/0275447 A1 | 11/2007 | Lewis et al. |
| 2008/0131945 A1 | 6/2008 | Toraya et al. |
| 2010/0330636 A1 | 12/2010 | Soucaille |

FOREIGN PATENT DOCUMENTS

| | | |
|---|---|---|
| CN | 87103534 A1 | 11/1988 |
| DE | 3734764 A1 | 5/1989 |
| EP | 0282474 A1 | 9/1988 |
| EP | 0305434 B1 | 3/1989 |
| EP | 0146075 B1 | 8/1989 |
| EP | 1204755 B1 | 8/2006 |
| FR | 2583060 A1 | 12/1986 |
| JP | 63102687 A1 | 5/1988 |
| JP | 63254986 A1 | 10/1988 |
| WO | 93/25696 A1 | 12/1993 |
| WO | 2001/04324 A1 | 1/2001 |
| WO | 03/104471 A1 | 12/2003 |
| WO | 2005/073364 A1 | 8/2005 |
| WO | 2005/116228 A2 | 12/2005 |
| WO | 2006/007530 A2 | 1/2006 |
| WO | 2006/117536 A1 | 11/2006 |
| WO | 2006/128381 A1 | 12/2006 |
| WO | 2006/131734 A1 | 12/2006 |
| WO | 2006/133637 A1 | 12/2006 |
| WO | 2007/030830 A2 | 3/2007 |
| WO | 2007/041269 A2 | 4/2007 |
| WO | 2007/130518 A2 | 11/2007 |
| WO | 2007/130521 A2 | 11/2007 |
| WO | 2007/140816 A1 | 12/2007 |
| WO | 2008/018930 A2 | 2/2008 |
| WO | 2008/025522 A1 | 3/2008 |

(Continued)

OTHER PUBLICATIONS

Papanikolaou, S., et al, The Effect of Raw Glycerol Concentration on the Production of 1,3-Propanediol by Clostridium Butyricum, Journal of Chemical Technology and Biotechnology, Nov. 2004:79(11):1189-96.

Gonzalez-Pajuelo, M., et al., Metabokic engineering of Clostridium acetobutylicum for the industrial production of 1,3-propanediol from glycerol, Metabolic Engineering, Sep. 2005;7(5-6):329-36.

Abbad-Andaloussi, S., et al., Properties of allyl alcohol-resistant mutants of Clostridium butyricum grown on glycerol, 1996;62(9):3499-3501.

Soni, B. K., et al, Continuous Acetone-Butanol Fermentation Influence of Vitamins on the Metabolic Activity of Clostridium-Acetobutylicum, Applied Microbiology and Biotechnology, 1987;27(1):1-5.

(Continued)

*Primary Examiner* — Sikarl Witherspoon
(74) *Attorney, Agent, or Firm* — Pepper Hamilton LLP (57) ABSTRACT

The present invention provides a method for the anaerobic production of 1,3 propanediol, by culturing a *Clostridium* strain in an appropriate culture medium comprising glycerol as a source of carbon, wherein said *Clostridium* strain does not produce substantially other products of the glycerol metabolism selected among the group consisting of: butyrate, lactate, butanol and ethanol, and recovering of 1,3-propanediol.

28 Claims, 1 Drawing Sheet

FOREIGN PATENT DOCUMENTS

| WO | 2008/072920 A1 | 6/2008 |
|---|---|---|
| WO | 2008/072921 A1 | 6/2008 |
| WO | 2008/074794 A1 | 6/2008 |
| WO | 2008/080124 A2 | 7/2008 |
| WO | 2008/040387 A1 | 10/2008 |

OTHER PUBLICATIONS

Green, E. M., et al., Genetic manipulation of acid formation pathways by gene inactivation in Clostridium acetobutylicum ATCC 824, Microbiology, Aug. 1996;142 ( Pt 8):2079-86.

Sambrook, J., et al., Molecular Cloning: A Laboratory Manual, 2nd ed., Cold Spring Harbor Lab., Cold Spring Harbor, New York, 1989.

Desai, R. P., et al., Metabolic flux analysis elucidates the importance of the acid-formation pathways in regulating solvent production by Clostridium acetobutylicum, Metab Eng., Jul. 1999:1(3):206-13.

Desai, R. P., et al., Antisense RNA strategies for metabolic engineering of Clostridium acetobutylicum, Appl Environ Microbiol., Mar. 1999;65(3):936-45.

Woods, D. R., The genetic engineering of microbial solvent production, Trends Biotechnol., Jul. 1995;13(7):259-64.

Green, E. M., et al., Genetic manipulation of acid and solvent formation in clostridium acetobutylicum ATCC 824, Biotechnol Bioeng., Apr. 5, 1998;58(2-3):215-21.

Harris, L. M., et al., Characterization of recombinant strains of the Clostridium acetobutylicum butyrate kinase inactivation mutant: need for new phenomenological models for solventogenesis and butanol inhibition?, Biotechnol Bioeng., Jan. 5, 2000;67(1):1-11.

Tummala, S. B., et al., Transcriptional analysis of product-concentration driven changes in cellular programs of recombinant Clostridium acetobutylicumstrains, Biotechnol Bioeng., Dec. 30, 2003;84(7):842-54.

Tummala, S. B., et al., Design of antisense RNA constructs for downregulation of the acetone formation pathway of Clostridium acetobutylicum, J Bacteriol., Mar. 2003;185(6):1923-34.

International Search Report dated Oct. 25, 2007.

International Search Report date Jun. 16, 2008.

Office Action dated Mar. 7, 2011 received in copending U.S. Appl. No. 12/447,726.

Durre et al., "New insights and novel developments in clostridial acetone/butanol/isopropanol fermentation," Appl Microbiol Biotechnol (1998) 49:639-648.

Liu et al., "Butyric acid and hydrogen production by Clostridium tyrobutyricum ATCC 25755 and mutants," Enzyme and Microbial Technol (2006) 38:521-528.

Final Office Action dated Aug. 19, 2011 received in copending U.S. Appl. No. 12/447,726.

Cary et al., "Cloning and expression of Clostridium acetobutylicum phosphotransbutyrylase and butyrate kinase genes in *Escherichia coli*," J Bacteriol (1988) 170(10):4613-4618.

Saint-Amans et al., "Regulation of carbon and electron flow in Clostridium butyricum VPI 3266 grown on glucose-glycerol mixtures." Journal Bacteriology (2001) 183(5):1748-1754.

PROCESS FOR THE BIOLOGICAL PRODUCTION OF 1,3-PROPANEDIOL FROM GLYCEROL WITH HIGH YIELD

CROSS-REFERENCE TO RELATED APPLICATIONS

This application is the U.S. National Stage filing of International Application Serial No. PCT/EP2006/067987 filed Oct. 31, 2006, which is incorporated herein by reference in its entirety.

FIELD OF INVENTION

The invention comprises a process for the bioconversion of glycerol to 1,3-propanediol at high yield by a metabolically engineered *Clostridium*.

BACKGROUND OF THE INVENTION 1,3-propanediol is a monomer use in the production of polyester fibers and with potential use in the manufacture of polyurethanes and cyclic compounds.

1,3-propanediol can be produced by different chemical routes from i) acrolein water and hydrogen ii) ethylene oxide carbon monoxide and water in the presence of phosphine and from glycerol and hydrogen in the presence of carbon monoxide. All these methods have in common to be expensive and to generate waste streams containing polluting substances.

1,3-propanediol can be produced as an acetate/butyrate/lactate/1,3-propanediol mixture by the fermentation of glycerol by different Clostridia. The general metabolism of glycerol into Clostridia is presented in FIG. 1.

Figure 1:
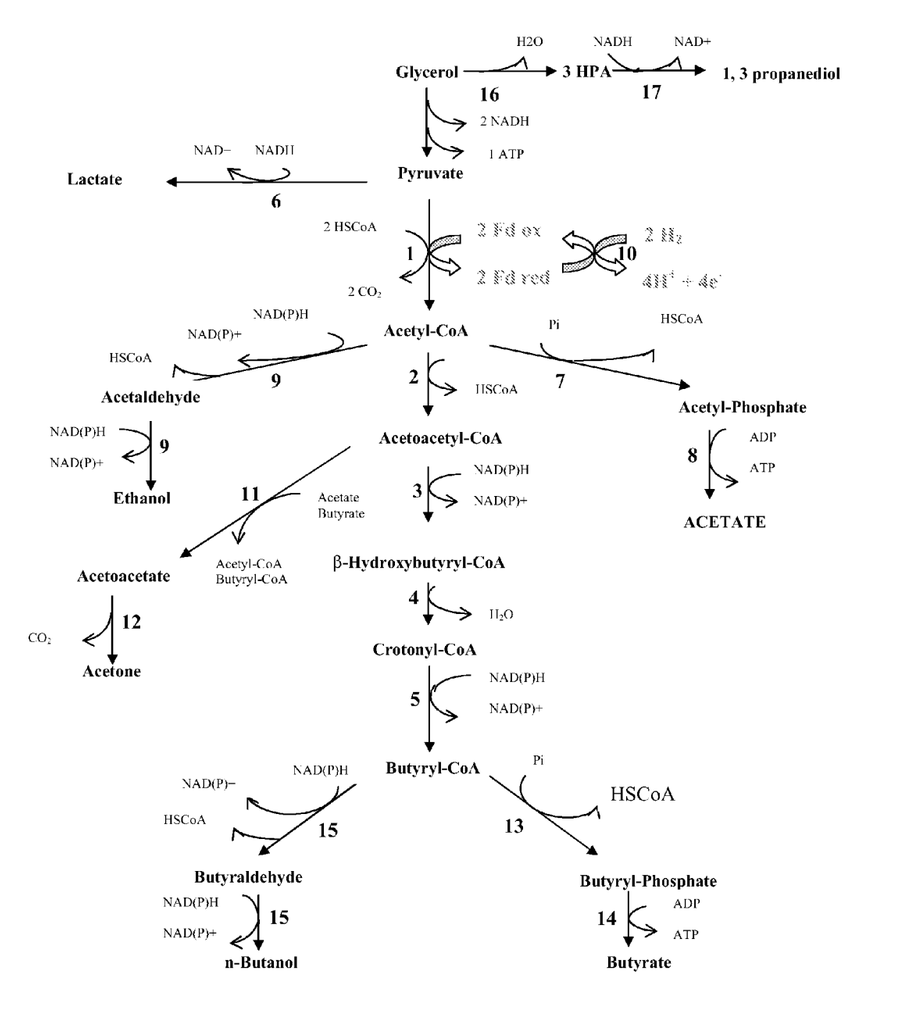

In one way, glycerol is converted to 1,3-propanediol in a two step enzymatic reaction sequence. In a first step a glycerol dehydratase catalyze the conversion of glycerol to 3-hydroxypropionaldehyde (3-HPA) and water. In the second step 3-HPA is reduced to 1,3-propanediol by a NADH dependent 1,3-propanediol dehydrogenase. Most of the 1,3-propanediol producing clostridia use a B12 dependent glycerol dehydratase encoded by the dhaB1B2B3 structural genes while *Clostridum butyricum* uses a B12 independent enzyme encoded by the dhaB1 structural gene. For the B12 dependent glycerol dehydratases, orfX and orfZ encode the glycerol dehydratase reactivation factor while for the only known B12 independent enzyme, dhaB2 encodes an S-Adenosyl-Méthionine (SAM) dependent activation factor. Near the genes encoding the structural and activation factors a gene encoding a 1,3-propanediol dehydrogenase (dhaT) is also present. Production of 1,3-propanediol from glycerol consumes NADH.

In another way, when glycerol is not transformed into 1,3-propanediol, it is oxidized to dihydrohycetone-phosphate (DHAP) with the concomitant production of NADH by either a glycerol kinase and a glycerol-3-Phosphate dehydrogenase encoded respectively by glpk and glpA or by a glycerol dehydrogenase followed by a DHA kinase encoded respectively by dhaD and dhaK1K2. DHAP will then enter the glycolitic pathway with the production of pyruvate and acetyl-CoA as key intermediates. Pyruvate and acetyl-CoA can be reduced to respectively lactate and ethanol by a lactate dehydrogenase encoded by the ldh gene and a bi-functional aldehyde-alcohol dehydrogenases encoded by adhE. Acetyl-CoA can also be converted to butyryl-CoA, an intermediate product that can be:

i) converted to butyric acid by a phospho-transbutyrylase and a butyrate kinase encoded respectively by the ptb and buk genes or ii) reduced to butanol by a bi-functional aldehyde-alcohol dehydrogenase encoded by adhE.

In solventogenic clostridia, acetone is produced from aceto-acetyl-CoA (an intermediate in the production of butyryl-CoA) by a CoA-transferase and an acetoacetate decarboxylase encoded respectively by the ctfAB and adc genes. Hydrogen is produced by an iron only hydrogenase encoded by the hydA gene.

Both natural and recombinant clostridia produce 1,3-propanediol at a maximal yield of 0.55 g/g of glycerol due to the co-production of reduced compounds like butyric acid (butyrate), lactic acid (lactate), ethanol or butanol. To increase the yield of 1,3-propanediol production it is necessary to avoid the production of all the reduced co-products and associate the production of 1,3-propanediol to an oxidized co-product.

*Clostridium acetobutylicum* strains unable to produce butyrate have already been described in the article (Green et al., 1996). The butyrate formation was dramatically reduced because of the inactivation of the buk gene obtained by single crossing-over with a non-replicable plasmid. This mutant strain was tested for the production of 1,3-propanediol as shown in (Gonzalez-Pajuelo, 2005, Metabolic Engineering). This recombinant strain effectively produces 1,3-propanediol as the main fermentation product, but produces also butanol, which decreases the 1,3-propanediol yield.

The 1,3-propanediol fermentation of glycerol by Clostridia can run in batch, fedbatch or continuous cultures.

The problem to be solved by the present invention is the biological production of 1,3 propanediol from glycerol at high yield, with no concomitant production of reduced compounds such as butyrate, lactate, or alcohols. This production is performed by anaerobic fermentation with *Clostridia*.

SUMMARY OF THE INVENTION

Applicants have solved the stated problem and the present invention provides a method for the anaerobic production of 1,3 propanediol, by culturing a *Clostridium* strain in an appropriate culture medium comprising glycerol as a source of carbon, wherein said *Clostridium* strain does not produce substantially other products of the glycerol metabolism selected among the group consisting of: butyrate, lactate, butanol and ethanol, and recovering 1,3-propanediol.

The 1,3-propanediol may be produced concomitantly with a single oxidized product of the glycerol metabolism.

In a particular aspect of the invention, the *Clostridium* strain is modified to limit production of metabolites from glycerol, which biosynthesis pathway is NADH or NADPH consuming, except for 1,3-propanediol.

In one aspect of this invention, a *Clostridium* naturally producing 1,3-propanediol is genetically modified to produce 1,3-propanediol at higher yield by deleting:

i) the gene coding for the butyrate kinase (buk) or the phospho-transbutyrylase (ptb) to avoid butyrate production ii) optionally, all the genes coding for the lactate dehydrogenases (ldh) to avoid lactate production iii) optionally, the genes coding for the bi-functional aldehyde-alcohol dehydrogenases (adhE) to avoid alcohols formation.

In another aspect of this invention, a *Clostridium* naturally producing butyrate but unable to produce 1,3-propanediol is genetically modified to produce 1,3-propanediol at high yield. This result is achieved by replacing the ptb or the buk genes coding for enzymes involved in the butyrate pathway with the operon of *C. butyricum* coding for enzymes involved in the B12 independent 1,3-propanediol pathway, and by deleting:

i) optionally, all the genes coding for the lactate dehydrogenases (ldh) to avoid lactate production ii) optionally, the genes coding for the bi-functionnal aldehyde-alcohol dehydrogenases (adhE) to avoid alcohols formation.

In a further aspect of this invention, a *Clostridum* naturally producing ethanol but unable to produce 1,3-propanediol is genetically modified to produce 1,3-propanediol. This result is achieved by replacing one of the adhE genes coding for enzymes involved in the ethanol pathway, with the operon of *C. butyricum* coding for enzymes involved in the B12 independent 1,3-propanediol pathway, and by deleting:

i) optionally, all the genes coding for the lactate dehydrogenase (ldh) to avoid lactate production ii) optionally, all the remaining genes coding for the bi-functionnal aldehyde-alcohol dehydrogenases (adhE) to avoid alcohol formation.

In another aspect of this invention, the flux of hydrogen production is decreased and then the flux of reducing equivalent is redirected toward 1,3-propanediol production by attenuating the gene encoding the hydrogenase (hydA).

In another aspect of the invention, the flux of 1,3-propanediol production is increased by introducing extra copies of the 1,3-propanediol operon from *C. butyricum*, (coding for enzymes involved in the B12 independent 1,3-propanediol pathway).

It is also an object of the present invention to provide a recombinant *Clostridum* strain, useful for the process of production of 1,3-propanediol at high yield.

BRIEF DESCRIPTION OF THE DRAWINGS

The accompanying drawing which is incorporated in and constitutes a part of this specification exemplifies the invention and together with the description, serve to explain the principles of this invention.

FIG. 1 depicts the central metabolism of different Clostridia.

1: Pyruvate-ferredoxin oxydoreductase; 2: Thiolase; 3: β-Hydroxybutyryl-CoA dehydrogenase; 4: Crotonase; 5: Butyryl-CoA dehydrogenase; 6: Lactate dehydrogenase; 7: Phospho-transacetylase; 8: Acetate kinase; 9: Acetaldehyde Ethanol deshydrogenase; 10: hydrogenase; 11: CoA transférase (Acetoacetyl-CoA:acetate/butyrate:CoA transferase); 12: Acetoacetate decarboxylase; 13: Phospho-transbutyrylase; 14: Butyrate kinase; 15: Butyraldehyde-Butanol dehydrogenase; 16: Glycerol dehydratase; 17: 1,3 propanediol dehydrogenase.

DETAILED DESCRIPTION OF THE INVENTION

As used herein the following terms may be used for interpretation of the claims and specification.

The terms "*Clostridium*" and "Clostridia" refer to all kind of bacteria belonging to this family.

An appropriate culture medium refers to a culture medium optimized for the growth and the diol production of the specifically used *Clostridium* strain.

The term "carbon substrate" or "source of carbon" means any carbon source capable of being metabolized by a microorganism wherein the substrate contains at least one carbon atom. In the present invention glycerol is the single source of carbon.

The phrase "microorganism is modified" means that the strain has been transformed in the aim to change its genetic characteristics. Endogenous genes can either be attenuated, deleted, or over-expressed. Exogenous genes can be introduced, carried by a plasmid, or integrated into the genome of the strain, to be expressed into the cell.

The term "attenuation" refers to a decreased expression of a gene or a decreased activity of the protein, product of the gene. The man skilled in the art knows numerous means to obtain this result, and for example:

Introduction of a mutation into the gene, decreasing the expression level of this gene, or the level of activity of the encoded protein.

Replacement of the natural promoter of the gene by a low strength promoter, resulting in a lower expression.

Use of elements destabilizing the corresponding messenger RNA or the protein.

Deletion of the gene if no expression is needed.

The term "deleted gene" means that a substantial part of the coding sequences of said gene was removed. Preferably, at least 50% of the coding sequence was removed, and more preferably at least 80%.

The term "plasmid" or "vector" as used herein refers to an extra chromosomal element often carrying genes which are not part of the central metabolism of the cell, and usually in the form of circular double-stranded DNA molecules.

In the description of the present invention, enzymes are identified by their specific activities. This definition thus includes all polypeptides that have the defined specific activity also present in other organisms, more particularly in other microorganisms. Often enzymes with similar activities can be identified by their grouping to certain families defined as PFAM or COG.

PFAM (protein families database of alignments and hidden Markov models; [[http://www.sanger.ac.uk/Software/Pfam/]] see world wide web at sanger.ac.uk/Software/Pfam/) represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins; [[http://www.ncbi.nlm.nih.gov/COG/]] see world wide web at ncbi.nlm.nih.gov/COG/) are obtained by comparing protein sequences from 43 fully sequenced genomes representing 30 major phylogenic lines. Each COG is defined from at least three lines, which permits the identification of former conserved domains.

The means of identifying homologous sequences and their percentage homologies are well known to those skilled in the art, and include in particular the BLAST programs, which can be used from the website [[http://www.ncbi.nlm.nih.gov/BLAST/]] (see world wide web at ncbi.nlm.nih.gov/BLAST/) with the default parameters indicated on that website. The sequences obtained can then be exploited (e.g., aligned) using, for example, the programs CLUSTALW [[(http://www.ebi.ac.uk/clustalw/)]] (see world wide web at ebi.ac.uk/clustalw/) or MULTALIN [[(http://prodes.toulouse.inra.fr/multalin/cgi-bin/multalin.p1)]] (see world wide web at prodes.toulouse.inralemultalin/cgi-bin/multalin.p1), with the default parameters indicated on those websites.

Using the references given on GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are described, for example, in Sambrook et al. (1989 Molecular Cloning: a Laboratory Manual. $2^{nd}$ ed. Cold Spring Harbor Lab., Cold Spring Harbor, N.Y.).

The present invention provides a method for the anaerobic production of 1,3-propanediol, by culturing a *Clostridium* strain in an appropriate culture medium comprising glycerol as a source of carbon, wherein said *Clostridium* strain does not produce substantially other products of the glycerol metabolism selected among the group consisting of: butyrate, lactate, butanol and ethanol, and recovering 1,3-propanediol.

"Substantially" means that at most traces of products or reductions of glycerol are found in the culture medium. Traces means preferably amounts that shall not interfere with the recovery process of 1,3-propanediol, more preferably less than 10 mM.

The phrase "glycerol metabolism" refers to all biochemical modifications of glycerol happening in the bacteria. This includes the biosynthesis of organic molecules (anabolism) and their breakdown (catabolism). Some metabolic reactions are consuming and some others are producing NADH/NADPH. Glycerol metabolism in *Clostridium* strains is illustrated in FIG. 1. Intermediates as well as final products from metabolic reactions are called metabolites.

The method of the invention is characterized by the fact that the glycerol metabolism is directed to 13,-propanediol production, and that no other reduced products from this metabolism pathway, such as butyrate, lactate, butanol, ethanol, are produced concomitantly with 1,3-propanediol by the *Clostridium*. Indeed, production of these reduced products is consuming NADH/NADPH stock of the cell. Limiting this consumption will allow the reducing power to be redirected toward 1,3-propanediol production.

In a specific embodiment of the invention, the 1,3-propanediol is produced concomitantly with a single oxidized product of glycerol metabolism, such as acetate, acetone or carbon dioxide. The term "oxidized product" refers to products produced without consumption of the NADH/NADPH stock of the cell Advantageously, the *Clostridium* strain used in the process produces only 1,3-propanediol and acetate.

According to the invention, the *Clostridium* strain can be modified to limit production of metabolites from glycerol, which biosynthesis pathway is NADH or NADPH consuming, except for 1,3-propanediol.

Advantageously, this modification consists of the deletion of at least one gene coding for an enzyme involved in production of said metabolites.

In particular, this enzyme is involved in the production of a metabolite selected among the group consisting of: butyrate, lactate, butanol and ethanol.

In a specific embodiment of the invention, the *Clostridium* is naturally producing 1,3-propanediol, since it comprises functional endogenous genes encoding for enzymes involved in biosynthesis of 1,3-propanediol. These genes are in particular: glycerol dehydratase and 1,3-propanediol dehydrogenase.

This strain can be genetically modified to produce 1,3-propanediol as major product by deleting at least one gene encoding for phospho-transbutyrylase (ptb) or butyrate kinase (buk) to block the conversion of butyryl-CoA to butyrate.

In another specific embodiment, said *Clostridium* said was also deleted of all the genes encoding for lactate dehydrogenase (ldh) to block the production of lactate.

In another specific embodiment, said *Clostridium* said was also deleted of all the genes encoding for bifunctionnal aldehyde-alcohol dehydrogenases (adhE) to block the production of alcohols.

Deletion of genes in Clostridia can be done using the method recently described in patent application PCT/EP2006/066997 allowing the i) replacement of the gene to delete with an erythromycin resistance gene and ii) removal of the erythromycin resistance gene by expressing the FLP recombinase.

Advantageously, the *Clostridium* strain is selected among the group consisting of *C. butyricum* and *C. pasteurianum*.

In a specific embodiment of the invention, the *Clostridium* strain has to be modified to be able to produce 1,3-propanediol. The modification consists of the introduction of at least one heterologous gene coding for an enzyme involved in the B-12 independent 1,3-propanediol pathway. These genes may be but are not limited to dhaB1, dhaB2, dhaT.

Advantageously, the strain is modified by introducing the operon of *Clostridium butyricum* coding for the enzymes involved in the B12-independent 1,3-propanediol pathway. Insertion of the operon in the chromosome can be done using the method recently described in patent application PCT/EP2006/066997.

In a specific embodiment of the invention, the used *Clostridum* strain naturally produces butyrate but is unable to produce 1,3-propanediol prior modification; this specific *Clostridium* is genetically modified to produce 1,3-propanediol by replacing at least one gene encoding for an enzyme involved in butyrate formation, in particular the phospho-transbutyrylase (ptb) or the butyrate kinase (buk), with one heterologous gene coding for an enzyme involved in the B-12 independent 1,3-propanediol pathway in the aim to:

- block the conversion of butyryl-CoA to butyrate and
- allow 1,3-propanediol production from glycerol in this strain.

Insertion of the operon in the chromosome and deletion of the genes can be done using the method recently described in patent application PCT/EP2006/066997.

Preferentially, in this *Clostridium* strain, all the genes encoding for lactate dehydrogenase (ldh) are deleted to block the production of lactate.

Preferentially, in this *Clostridium* strain, all the genes encoding for bi-functional aldehyde-alcohol dehydrogenases (adhE) are deleted, to inhibit the production of alcohols.

Advantageously, this *Clostridium* strain is selected among the group consisting of *C. acetobutylicum, C. beijerinckii, C. saccharoperbutylacetonicum C. saccharobutylicum, C. butyricum* or *C. cellulolyticum.*

In a specific embodiment of the invention, the *Clostridum* naturally produces ethanol but is unable to produce 1,3-propanediol prior modification; this strain is genetically modified to produce 1,3-propanediol by replacing at least one gene encoding for bi-functional aldehyde-alcohol dehydrogenases (adhE) with at least one of the heterologous gene coding for an enzyme involved in the B12 independent 1,3-propanediol pathway. Preferentially this heterologous gene is the operon of *C. butyricum* encoding for enzymes involved in the B12 independent 1,3-propanediol pathway.

This replacement leads to:

- a decrease of the conversion of acetyl-CoA to ethanol, and
- 1,3-propanediol production from glycerol.

Preferably, in this *Clostridium* strain, all the genes encoding for lactate dehydrogenase (ldh) are deleted to inhibit the production of lactate.

Preferably, in this *Clostridium* strain, all the remaining genes encoding for bi-functional aldehyde-alcohol dehydrogenases (adhE) are deleted to block the production of alcohols.

Insertion of the operon in the *Clostridium* chromosome and deletion of the previously cited genes can be done using the method recently described in patent application PCT/EP2006/066997.

Advantageously, this *Clostridium* strain is selected among the group consisting of *Clostridium thermocellum*, *Clostridium saccharolyticum* (now *Thermoanaerobacter saccharolyticum*), *Clostridium thermosulfurogenes* (now *Thermoanaerobacter thermosulfurigenes*) or *Clostridium thermohydrosulfuricum* (now *Thermoanaerobacter ethanolicus*).

In a specific embodiment of the invention, the *Clostridium* strain has a decreased flux of hydrogen production and consequently presents a redirection of the flux of reducing equivalent toward 1,3-propanediol production. This result may be achieved by various means, and in particular by attenuating the gene encoding the hydrogenase (hydA), an enzyme that provides a sink for reducing equivalent in the form of hydrogen production. Attenuation of hydA can be done by replacing the natural promoter by a low strength promoter or by using an element destabilizing the corresponding messenger RNA or the protein. If needed, complete attenuation of the gene can also be achieved by partial or complete deletion of the corresponding DNA sequence.

In another embodiment of the invention, the used *Clostridium* strain presents an increased flux of 1,3-propanediol production; this result is achieved by introducing extra copies of the 1,3-propanediol operon from *C. butyricum*, (coding for enzymes involved in the B12 independent 1,3-propanediol pathway) either over-expressed by a plasmid or integrated into the chromosome of the recombinant *Clostridium*. For example the pSPD5 plasmid can be used for an over-expression of the 1,3-propanediol operon.

In another aspect of the invention, the *Clostridium* strain is modified to be able to convert acetate to acetone. This modification can be obtained by introducing into the microorganism an artificial "acetone operon" containing the thl, ctfAB and adc genes coding respectively for the thiolase, the CoA-transferase and the aceto-acetate decarboxylase, these three enzymes being involved in acetone formation in *C. acetobutylicum* and *C. beijerinckii*. This artificial operon can be either carried by a plasmid or can be integrated into the chromosome of the transformed *Clostridium*.

In another embodiment, the invention provides a method for the fermentative preparation of 1,3-propanediol at high yield, comprising:

(a) contacting a *Clostridium* strain with glycerol for a fermentation process whereby 1,3-propanediol is produced, (b) isolating 1,3-propanediol and optionally a single oxidized product of the glycerol metabolism (mainly acetate or acetone) by distillation.

The fermentation is generally conducted in fermentors with an inorganic culture medium of known defined composition adapted to the bacteria used, containing at least glycerol, and if necessary a co-substrate necessary for the production of the metabolite.

This process can be realized in a batch process as well as in a continuous process. The man skilled in the art knows how to manage each of these experimental conditions, and to define the culture conditions for the microorganisms according to the invention. In particular the clostridia are fermented at a temperature between 20° C. and 60° C., preferentially between 25° C. and 40° C. for mesophilic clostridia and between 45 and 60° C. for thermophilic Clostridia.

The invention is also related to the microorganism as described previously. Preferably, this microorganism is selected among the group consisting of *C. butyricum, C. pasteurianum, C. acetobutylicum, C. beijerinckii, C. saccharoperbutylacetonicum C. saccharobutylicum, C. butyricum, C. cellulolyticum, Clostridium thermocellum, Clostridium saccharolyticum* (now *Thermoanaerobacter saccharolyticum*), *Clostridium thermosulfurogenes* (now *Thermoanaerobacter thermosulfurigenes*) or *Clostridium thermohydrosulfuricum* (now *Thermoanaerobacter ethanolicus*).

EXAMPLE 1

Construction of a Recombinant *Clostridium Acetobutylicum* Producing 1,3-Propanediol and Unable to Produce Butyrate and Butanol: *C. Acetobutylicum* ΔpSOL1 Δcac1515 Δupp Δbuk::PDO To obtain a strain that can be genetically manipulated and is unable to produce butanol and acetone, we first cure the pSOL1 megaplasmid from the *C. acetobutylicum* Δcac1515 Δupp strain (described in patent application PCT/EP2006/066997) by i) running 20 sub-cultures in glucose MS medium and ii) by selection on agar plates (containing starch (2%) and glucose (0.2%) as described by Sabathe et al (2003)) of clones producing small hallo of starch hydrolysis to identify a *C. acetobutylicum* ΔpSOL1 Δcac1515 Δupp strain. To delete the buk gene and introduce the 1,3-propanediol operon from *C. butyricum*, the homologous recombination strategy described by Croux & Soucaille (2006) in patent application PCT/EP2006/066997 is used. A buk deletion cassette integrating the 1,3-propanediol operon from *C. butyricum* in the pCons::upp vector was constructed as follows.

Two DNA fragments surrounding buk were PCR amplified with the Pwo polymerase with total DNA from *C. acetobutylicum* as template and two specific couples of olignonucleotides. With the couples of primers BUK 1-BUK 21 and BUK 31-BUK 4, two DNA fragments were respectively obtained. Both primers BUK 1 and BUK 4 introduce a BamHI site while primers BUK 21 and BUK 31 have a complementary region which introduces pvuII and NruI sites. DNA fragments BUK 1-BUK 21 and BUK 31-BUK 4 were joined in a PCR fusion experiment with primers BUK 1 and BUK 4 and the resulting fragment was cloned in pCR4-TOPO-Blunt to yield pTOPO:buk. At the unique nruI site of pTOPO:buk, an antibiotic resistance MLS gene with FRT sequences on both sides was introduced from the 1372 bp StuI fragment of pUC18-FRT-MLS2. The BUK deletion cassette obtained after BamHI digestion of the resulting plasmid was cloned into pCons::upp at the BamHI site to yield the pREPΔBUK::upp plasmid. At the unique pvuII site of pREPΔBUK::upp, the 1,3-propanediol operon was introduced as a 4854 bp blunt end Klenow treated SalI fragment of pSPD5 plasmid.

The pREPΔBUK::PDO::upp plasmid was used to transform by electroporation *C. acetobutylicum* ΔpSOL1 Δcac15Δupp strain. After selection on Petri plate for clones resistant to erythromycin (40 μg/ml), one colony was cultured for 24 hours in Glycerol liquid synthetic medium with erythromycin at 40 μg/ml and 100 μl of undiluted culture was plated on RCGA (Reinforced *Clostridium* medium where starch and glucose are replaced by glycerol as a carbon source) with erythromycin at 40 μg/ml and 5-FU at 400 μM. Colonies resistant to both erythromycin and 5-FU were replica plated on both RCA with erythromycin at 40 μg/ml and RCA with thiamphenicol at 50 μg/ml to select clones where 5-FU resistance is also associated with thiamphenicol sensitivity. The genotype of clones resistant to erythromycin and sensitive to thiamphenicol was checked by PCR analysis (with primers BUK 0 and BUK 5 located outside of the buk deletion cassette).

The ΔpSOL1Δcac15ΔuppΔbuk::PDO::mls$^R$ strain which have lost pREPΔbuk::upp was isolated.

The ΔpSOL1Δcac15ΔuppΔbuk::PDO::mls$^R$ strain was transformed with pCLF1.1 vector expressing the Flp1 gene encoding the Flp recombinase from S. cerevisiae. After transformation and selection for resistance to thiamphenicol (50 μg/ml) on Petri plate, one colony was cultured on synthetic liquid medium with thiamphenicol at 50 μg/ml and appropriate dilutions were plated on RCA with thiamphenicol at 50 μg/ml. Thiamphenicol resistant clones were replica plated on both RCA with erythromycin at 40 μg/ml and RCA with thiamphenicol at 50 μg/ml. The genotype of clones with erythromycin sensitivity and thiamphenicol resistance was checked by PCR analysis with primers BUK 0 and BUK 5. Two successive 24 hours cultures of the Δcac15ΔuppΔbuk strain with erythromycin sensitivity and thiamphenicol resistance were carried out in order to lose pCLF1.1. The ΔpSOL1Δcac15ΔuppΔbuk::PDO strain which has lost pCLF1.1 was isolated according to its sensitivity to both erythromycin and thiamphenicol.

LDH 3 have a complementary region which introduces a StuI site. DNA fragments LDH 1-LDH 2 and LDH 3-LDH 4 were joined in a PCR fusion experiment with primers LDH 1 and LDH 4 and the resulting fragment was cloned in pCR4-TOPO-Blunt to yield pTOPO:LDH. At the unique StuI site of pTOPO:LDH, an antibiotic resistance MLS gene with FRT sequences on both sides was introduced from the 1372 bp StuI fragment of pUC18-FRT-MLS2. The UPP deletion cassette obtained after BamHI digestion of the resulting plasmid was cloned into pCons::upp at the BamHI site to yield the pREP-ΔLDH::upp plasmid.

The pREPALDH::upp plasmid was used to transform by electroporation C. acetobutylicum ΔpSOL1Δcac15ΔuppΔbuk::PDO strain. After selection on Petri plate (on RCGA) for clones resistant to erythromycin (40 μg/ml), one colony was cultured for 24 hours in liquid glycerol synthetic medium with erythromycin at 40 μg/ml and 100 μl of undiluted culture was plated on RCGA with erythromycin at 40 μg/ml and 5-FU at 400 μM. Colonies resistant to both erythromycin and 5-FU were replica plated on both RGCA with erythromycin at 40 μg/ml and RGCA with thiamphenicol at 50 μg/ml to select clones where 5-FU resistance is also associated with thiamphenicol sensitivity. The genotype of clones resistant to erythromycin and sensitive to thiamphenicol was checked by PCR analysis (with primers LDH 0 and LDH 5 located outside of the ldh deletion cassette). The ΔΔpSOL1Δcac15ΔuppΔbuk::PDOΔldh::mls$^R$ strain which have lost pREPΔLDH::upp was isolated.

TABLE 1

| Name | Primer sequences |
|---|---|
| Buk 1 | aaaaggatcctagtaaaagggagtgtacgaccagtg |
| Buk 21 | gggcagctggtcgcgaaaaaggggggattattagtaatctatacatgttaacattcctccac |
| Buk 31 | ccccttcttcgcgaccagctgccccacttcttgcacttgcagaaggtggac |
| Buk 4 | aaaaggatcctctaaattctgcaatatatgcccccc |
| Buk 0 | ataacaggatatatgctctctgacgcgg |
| Buk 5 | gatcatcactcattttaaacatggggcc |

EXAMPLE 2

Construction of Strains unable to Produce Butyrate, Acetone and Lactate: C. Acetobutylicum ΔpSOL1 Δcac1515 Δupp Δbuk::PDO Δldh To delete the ldh gene, the homologous recombination strategy described by Croux & Soucaille (2006) in patent application PCT/EP2006/066997 is used. This strategy allows the insertion of an erythromycin resistance cassette, while deleting most of the genes concerned. The ldh deletion cassette in pCons::upp was constructed as follows.

Two DNA fragments surrounding ldh (CAC267) were PCR amplified with the Pwo polymerase with total DNA from C. acetobutylicum as template and two specific couples of oligonucleotides. With the couples of primers LDH 1-LDH 2 and LDH 3-LDH 4, 1135 bp and 1177 bp DNA fragments were respectively obtained. Both primers LDH 1 and LDH 4 introduce a BamHI site while primers LDH 2 and The ΔpSOL1Δcac15ΔuppΔbuk::PDOΔldh::mls$^R$ strain was transformed with pCLF1.1 vector expressing the Flp1 gene encoding the Flp recombinase from S. cerevisiae. After transformation and selection for resistance to thiamphenicol (50 μg/ml) on Petri plate, one colony was cultured on synthetic liquid medium with thiamphenicol at 50 μg/ml and appropriate dilutions were plated on RCA with thiamphenicol at 50 μg/ml. Thiamphenicol resistant clones were replica plated on both RCA with erythromycin at 40 μg/ml and RCA with thiamphenicol at 50 μg/ml. The genotype of clones with erythromycin sensitivity and thiamphenicol resistance was checked by PCR analysis with primers LDH 0 and LDH 5. Two successive 24 hours cultures of the ΔpSOL1Δcac15ΔuppΔbuk::PDOΔldh strain with erythromycin sensitivity and thiamphenicol resistance were carried out in order to lose pCLF1.1. The ΔpSOL1Δcac15ΔuppΔbuk::PDOΔldh strain which has lost pCLF1.1 was isolated according to its sensitivity to both erythromycin and thiamphenicol.

TABLE 2

| Name | Primer sequences |
|---|---|
| Ldh 1 | AAAAGGATCCGCTTTAAAATTTGGAAAGAGGAAGTTGTG |
| Ldh 2 | GGGGAGGCCTAAAAAGGGGGTTAGAAATCTTTAAAAATTTCTCTATAGAGCCCATC |
| Ldh 3 | CCCCCTTTTTAGGCCTCCCCGGTAAAAGACCTAAACTCCAAGGGTGGAGGCTAGGT |
| Ldh 4 | AAAAGGATCCCCCATTGTGGAGAATATTCCAAAGAAGAAAATAATTGC |
| Ldh 0 | CAGAAGGCAAGAATGTATTAAGCGGAAATGC |
| Ldh 5 | CTTCCCATTATAGCTCTTATTCACATTAAGC |

EXAMPLE 3

Construction of Strains with Lower Hydrogen Production: C. Acetobutylicum ΔpSOL1 Δcac1515 Δupp Δbuk::PDO Δldh ΔhydA To delete the hydA gene, the homologous recombination strategy described by Croux & Soucaille (2006) in patent application PCT/EP2006/066997 is used. This strategy allows the insertion of an erythromycin resistance cassette, while deleting most of the genes concerned. The hydA deletion cassette in pCons::upp was constructed as follows. Two DNA fragments surrounding hydA (CACO28) were PCR amplified with the Pwo polymerase with total DNA from C. acetobutylicum as template and two specific couples of olignonucleotides. With the couples of primers HYD 1-HYD 2 and HYD 3-HYD 4, 1269 bp and 1317 bp DNA fragments were respectively obtained. Both primers HYD 1 and HYD 4 introduce a BamHI site while primers HYD 2 and HYD 3 have a complementary region which introduces a StuI site. DNA fragments HYD 1-HYD 2 and HYD 3-HYD 4 were joined in a PCR fusion experiment with primers HYD 1 and HYD 4 and the resulting fragment was cloned in pCR4-TOPO-Blunt to yield pTOPO:HYD. At the unique StuI site of pTOPO:HYD, an antibiotic resistance MLS gene with FRT sequences on both sides was introduced from the 1372 bp StuI fragment of pUC18-FRT-MLS2. The UPP deletion cassette obtained after BamHI digestion of the resulting plasmid was cloned into pCons::upp at the BamHI site to yield the pREP-ΔHYD::upp plasmid.

The pREPΔHYD::upp plasmid was used to transform by electroporation C. acetobutylicum ΔpSOL1Δcac15ΔuppΔbuk::PDOΔldh strain. After selection on Petri plate (RCGA) for clones resistant to erythromycin (40 μg/ml), one colony was cultured for 24 hours in glycerol liquid synthetic medium with erythromycin at 40 μg/ml and 100 μl of undiluted culture was plated on RCA with erythromycin at 40 μg/ml and 5-FU at 400 μM. Colonies resistant to both erythromycin and 5-FU were replica plated on both RCGA with erythromycin at 40 μg/ml and RCA with thiamphenicol at 50 μg/ml to select clones where 5-FU resistance is also associated with thiamphenicol sensitivity. The genotype of clones resistant to erythromycin and sensitive to thiamphenicol was checked by PCR analysis (with primers HYD 0 and HYD 5 located outside of the hydA deletion cassette). The ΔpSOL1Δcac15ΔuppΔbuk::PDOΔldhΔhydA::mls$^R$ strain which have lost pREPΔHYD::upp was isolated.

The ΔpSOL1Δcac15ΔuppΔbuk::PDOΔldhΔhydA::mls$^R$ strain was transformed with pCLF1.1 vector expressing the Flp1 gene encoding the Flp recombinase from S. cerevisiae. After transformation and selection for resistance to thiamphenicol (50 μg/ml) on Petri plate, one colony was cultured on synthetic liquid medium with thiamphenicol at 50 μg/ml and appropriate dilutions were plated on RCA with thiamphenicol at 50 μg/ml. Thiamphenicol resistant clones were replica plated on both RCA with erythromycin at 40 μg/ml and RCA with thiamphenicol at 50 μg/ml. The genotype of clones with erythromycin sensitivity and thiamphenicol resistance was checked by PCR analysis with primers HYD 0 and HYD 5. Two successive 24 hours cultures of the ΔpSOL1Δcac15ΔuppΔbuk::PDOΔldhΔhydA strain with erythromycin sensitivity and thiamphenicol resistance were carried out in order to lose pCLF1.1. The ΔpSOL1Δcac15ΔuppΔbuk::PDOΔldhΔhydA strain which has lost pCLF1.1 was isolated according to its sensitivity to both erythromycin and thiamphenicol.

TABLE 3

| Name | Primer sequences |
|---|---|
| Hyd 1 | AAAA(illegible)GCCTCTTCTGTATTATGCAAGGAAAGCAGCTGC |
| Hyd 2 | GGGGAGGCCTAAAAAGGGGGTATATAAAATAAATGTGCCTTAACATCTAAGTTGAGGCC |
| Hyd 3 | CCCCCTTTTTAGGCCTCCCCGTTTATCCTCCCAAAATGTAAAATATAATTAAAATATATTAATAAACTTCGATTAATAAACTTCG |
| Hyd 4 | AAAAGGATCCCCTTTTAGCGTATAAAGTTTTATATAGCTATTG |
| Hyd 0 | CATGTTCTATTGTTACTATGGAAGAGGTAGTAG |
| Hyd 5 | GCAGTTATTATAAATGCTGCTACTAGAGC |

EXAMPLE 4

Construction of Strains with Increase Flux in the 1,3-Propanediol Pathway: C. acetobutylicum ΔpSOL1 Δcac1515 Δupp Δbuk::PDO Δldh pSPD5

To construct a strain that converts glycerol to 1,3-propanediol and acetate at higher flux we introduce the pSPD5 plasmid (described in patent application WO01/04324) that expressed as an operon the B12 independent 1,3-propanediol pathway from C. butyricum. The pSPD5 plasmid was used to transform by electroporation of C. acetobutylicum ΔpSOL1Δcac15ΔuppΔbuk::PDOΔldh strain. After selection on Petri plate (RCGA) for clones resistant to erythromycin (40 µg/ml), one colony was cultured for 24 hours in glycerol liquid synthetic medium with erythromycin at 40 µg/ml and use to extract the pSPD5 plasmid that was characterized by its restriction profile.

EXAMPLE 5

Construction of Strains Producing 1,3-propanediol and Acetone: *C. Acetobutylicum* ΔpSOL1 Δcac1515 Δupp Δbuk::PDO Δldh pSOS95 thl To construct a strain that converts acetate to acetone the pSOS 95 thl plasmid expressing a synthetic acetone operon was constructed. For this purpose the thl gene encoding thiolase (from *C. acetobutylicum*) was introduced at the BamHI site of the pSOS95 vector (genbank accession n° AY187686) already expressing as a synthetic operon the ctfAB and adc genes. The thl gene was PCR amplified with the Pwo polymerase with total DNA from *C. acetobutylicum* as template and two specific couples of olignonucleotides. With the couple of primers THL 1-THL2 a 1.2 kbp DNA fragment was obtained and digested with BamHI and Bg1II, two restriction sites that were respectively introduced by primers THL 1 and THL2. After ligation to the BamhI digested pSOS95, the pSOS95-thl plasmid was obtained.

This pSOS95-thl plasmid was used to transform by electroporation *C. acetobutylicum* ΔpSOL1Δcac15ΔuppΔbuk::PDOΔldh strain. After selection on Petri plate (RCGA) for clones resistant to erythromycin (40 μg/ml), one colony was cultured for 24 hours in glycerol liquid synthetic medium with erythromycin at 40 μg/ml and use to extract the pSOS95-thl plasmid that was characterized by its restriction profile.

TABLE 4

| Name | Primer sequences |
|---|---|
| THL 1 | cgc ggatcc tttatctgttaccccgtatcaaaatttagg |
| THL 2 | ga AGATCT TCTAGCACTTTTCTAGCAATATTGC |

EXAMPLE 6

Batch Fermentation of 1,3-Propanediol Producing Strains

Strains were initially analyzed in anaerobic flask cultures in the synthetic medium described by Soni et al (Soni et al, 1986, *Appl. Microbiol. Biotechnol.* 32:120-128) supplemented with 2.5 g/1 of ammonium acetate and with replacement of glucose by glycerol. An overnight culture at 35° C. was used to inoculate a 30 ml culture to an OD600 of 0.05. After incubation of the culture for 3 days at 35° C., glycerol, organic acids and 1,3-propanediol were analyzed by HPLC using a Biorad HPX 97H column for the separation and a refractometer for the detection.

Strains with the correct phenotype were subsequently tested under production conditions in 300 ml fermentors (DASGIP) using an anaerobic batch protocol.

For this purpose the fermentor was filled with 250 ml of synthetic medium, sparged with nitrogen for 30 min and inoculated with 25 ml of preculture to an optical density (OD600nm) between 0.05 and 0.1.

The temperature of the culture was maintained constant at 35° C. and the pH was permanently adjusted at 6.5 using an $NH_4OH$ solution. The agitation rate was maintained at 300 rpm during the fermentation.

EXAMPLE 7

Continuous Fermentation of 1,3-Propanediol and Acetate Producing Strains

The best 1,3-propanediol and acetate producing strain was analyzed in chemostat cultures in the synthetic medium described by Soni et al (Soni et al, 1987, *Appl. Microbiol. Biotechnol.*) except that glucose was replaced by glycerol. An overnight culture at 35° C. was used to inoculate a 300 ml fermentors (DASGIP) using an anaerobic chemostat protocol.

For this purpose the fermentor was filled with 250 ml of synthetic medium, sparged with nitrogen for 30 min and inoculated with 25 ml of preculture to an optical density (OD600nm) between 0.05 and 0.1. After 12 hours of batch culture at 35° C., pH 6.5 (regulated using an $NH_4OH$ solution) and an agitation rate of 300 rpm, the fermentor was continuously fed with oxygen free synthetic medium at a dilution rate of 0.05 h-1 while the volume was kept constant by sequential removal of fermentated medium. Stability of the culture was followed by products analysis using the HPLC protocol previously described.

REFERENCES

Gonzalez-Pajuelo M, Meynial-Salles I, Mendes F, Andrade J C, Vasconcelos I, Soucaille P.

Metabolic engineering of *Clostridium acetobutylicum* for the industrial production of 1,3-propanediol from glycerol.

Metab Eng. 2005; 7:329-36.

Green E M, Boynton Z L, Harris L M, Rudolph F B, Papoutsakis E T, Bennett G N.

Genetic manipulation of acid formation pathways by gene inactivation in *Clostridium acetobutylicum* ATCC 824.

Microbiology. 1996, 142:2079-86.

Soni B. K., Soucaille P. Goma G.

Continuous acetone butanol fermentation: influence of vitamins on the metabolic activity of *Clostridium acetobutylicum.*

Appl. Microbiol. Biotechnol. 1987. 27:1-5.

The invention claimed is:

1. A method for the anaerobic production of 1,3-propanediol comprising:
    culturing a *Clostridium* strain in an appropriate culture medium comprising glycerol as a source of carbon; and recovering 1,3-propanediol,
    wherein said *Clostridium* strain does not produce substantially other products of the glycerol metabolism selected from: butyrate, lactate, butanol and ethanol;
    wherein the *Clostridium* strain produces only 1,3-propanediol and acetate from glycerol;
    wherein the *Clostridium* strain comprises functional endogenous genes for production of 1,3-propanediol; and
    wherein all the ldh genes coding for lactate dehydrogenases are deleted.

2. A method for the anaerobic production of 1,3-propanediol comprising:
    culturing a *Clostridium* strain in an appropriate culture medium comprising glycerol as a source of carbon; and recovering 1,3-propanediol,
    wherein said *Clostridium* strain does not produce substantially other products of the glycerol metabolism selected from: butyrate, lactate, butanol and ethanol;
    wherein the *Clostridium* strain produces only 1,3-propanediol and acetate from glycerol;
    wherein the *Clostridium* strain comprises functional endogenous genes for production of 1,3-propanediol; and
    wherein all the adhE genes coding for aldehyde-alcohol dehydrogenases are deleted.

3. The method according to claim 1 or 2 wherein the *Clostridium* strain is selected from *C. butyricum* and *C. pasteurianum*.

4. A method for the anaerobic production of 1,3-propanediol comprising:
    culturing a *Clostridium* strain in an appropriate culture medium comprising glycerol as a source of carbon; and recovering 1,3-propanediol;
    wherein said *Clostridium* strain does not produce substantially other products of the glycerol metabolism selected from: butyrate, lactate, butanol and ethanol;
    wherein the *Clostridium* strain produces only 1,3-propanediol and acetate from glycerol;
    wherein the *Clostridium* strain is modified to produce 1,3-propanediol by introducing at least one heterologous gene coding for an enzyme involved in the B-12 independent 1,3-propanediol pathway;
    wherein the *Clostridium* strain, prior to modification, can produce butyrate and the at least one heterologous gene is introduced to replace at least one gene coding for an enzyme involved in butyrate formation;
    wherein the gene coding for an enzyme involved in butyrate formation is ptb encoding phospho-transbutyrylase or buk encoding butyrate kinase; and
    wherein all the ldh genes coding for lactate dehydrogenases are deleted.

5. A method for the anaerobic production of 1,3-propanediol comprising:
    culturing a *Clostridium* strain in an appropriate culture medium comprising glycerol as a source of carbon; and recovering 1,3-propanediol;
    wherein said *Clostridium* strain does not produce substantially other products of the glycerol metabolism selected from: butyrate, lactate, butanol and ethanol;
    wherein the *Clostridium* strain produces only 1,3-propanediol and acetate from glycerol;
    wherein the *Clostridium* strain is modified to produce 1,3-propanediol by introducing at least one heterologous gene coding for an enzyme involved in the B-12 independent 1,3-propanediol pathway;
    wherein the *Clostridium* strain, prior to modification, can produce butyrate and the at least one heterologous gene is introduced to replace at least one gene coding for an enzyme involved in butyrate formation; and
    wherein all the adhE genes coding for aldehyde-alcohol dehydrogenases are deleted.

6. The method according to claim 4 or 5 wherein the *Clostridium* strain is selected from *C. acetobutylicum, C. beijerinckii, C. saccharoperbutylacetonicum, C. saccharobutylicum, C. butyricum* and *C. cellulolyticum*.

7. A method for the anaerobic production of 1,3-propanediol comprising:
    culturing a *Clostridium* strain in an appropriate culture medium comprising glycerol as a source of carbon; and recovering 1,3-propanediol;
    wherein said *Clostridium* strain does not produce substantially other products of the glycerol metabolism selected from: butyrate, lactate, butanol and ethanol;
    wherein the *Clostridium* strain produces only 1,3-propanediol and acetate from glycerol;
    wherein the *Clostridium* strain is modified to produce 1,3-propanediol by introducing at least one heterologous gene coding for an enzyme involved in the B-12 independent 1,3-propanediol pathway; and
    wherein the *Clostridium* strain, prior to modification, can produce ethanol and the at least one heterologous gene is introduced to replace at least one gene coding for an enzyme involved in ethanol formation.

8. The method of claim 7, wherein the gene coding for an enzyme involved in ethanol formation is selected among the adhE genes coding for aldehyde-alcohol dehydrogenases.

9. The method according to claim 8 wherein all the ldh genes coding for lactate dehydrogenases are deleted.

10. The method according to claim 7 wherein all the remaining adhE genes coding for aldehyde-alcohol dehydrogenases are deleted.

11. The method according to claim 7 wherein the *Clostridium* strain is selected from *Clostridium thermocellum, Clostridium saccharolyticum* (now *Thermoanaerobacter saccharolyticum*), *Clostridium thermosulfurogenes* (now *Thermoanaerobacter thermosulfurigenes*) and *Clostridium thermohydrosulfuricum* (now *Thermoanaerobacter ethanolicus*).

12. A method for the anaerobic production of 1,3-propanediol comprising:
  culturing a *Clostridium* strain in an appropriate culture medium comprising glycerol as a source of carbon; and recovering 1,3-propanediol;
  wherein said *Clostridium* strain does not produce substantially other products of the glycerol metabolism selected from: butyrate, lactate, butanol and ethanol;
  wherein the *Clostridium* strain produces only 1,3-propanediol and acetate from glycerol;
  wherein the microorganism is modified to decrease the hydrogen flux and to re-direct the reducing power to 1,3-propanediol production; and
  wherein the hydA gene involved in the hydrogen flux is attenuated.

13. A method for the anaerobic production of 1,3-propanediol comprising:
  culturing a *Clostridium* strain in an appropriate culture medium comprising glycerol as a source of carbon; and recovering 1,3-propanediol;
  wherein said *Clostridium* strain does not produce substantially other products of the glycerol metabolism selected from: butyrate, lactate, butanol and ethanol;
  wherein the *Clostridium* strain produces only 1,3-propanediol and acetate from glycerol; and
  wherein the microorganism is modified to convert acetate to acetone.

14. The method as claimed in claim 13 wherein the genes coding for the enzymes involved in acetone formation are exogenous and are introduced into the *Clostridium* strain.

15. A 1,3-propanediol-producing *Clostridium* strain, wherein the strain does not produce substantially other products of the glycerol metabolism chosen from butyrate, lactate, butanol, and ethanol, wherein the strain comprises functional endogenous genes for production of 1,3-propanediol, and wherein all the ldh genes coding for lactate dehydrogenases are deleted.

16. A 1,3-propanediol-producing *Clostridium* strain, wherein the strain does not produce substantially other products of the glycerol metabolism chosen from butyrate, lactate, butanol, and ethanol, wherein the strain comprises functional endogenous genes for production of 1,3-propanediol, and wherein all the adhE genes coding for aldehyde-alcohol dehydrogenases are deleted.

17. The *Clostridium* strain of claim 15 or claim 16, wherein the strain is *C. butyricum* or *C. pasteurianum*.

18. A 1,3-propanediol-producing *Clostridium* strain,
  wherein the strain does not produce substantially other products of the glycerol metabolism chosen from butyrate, lactate, butanol, and ethanol;
  wherein the strain is modified to produce 1,3-propanediol by introducing at least one heterologous gene coding for an enzyme involved in the B-12 independent 1,3-propanediol pathway;
  wherein the strain, prior to modification, can produce butyrate and the at least one heterologous gene is introduced to replace at least one gene coding for an enzyme involved in butyrate formation;
  wherein the gene coding for an enzyme involved in butyrate formation is ptb encoding phospho-transbutyrylase or buk encoding butyrate kinase; and
  wherein all the ldh genes coding for lactate dehydrogenases are deleted.

19. A 1,3-propanediol-producing *Clostridium* strain,
  wherein the strain does not produce substantially other products of the glycerol metabolism chosen from butyrate, lactate, butanol, and ethanol;
  wherein the strain is modified to produce 1,3-propanediol by introducing at least one heterologous gene coding for an enzyme involved in the B-12 independent 1,3-propanediol pathway;
  wherein the strain, prior to modification, can produce butyrate and the at least one heterologous gene is introduced to replace at least one gene coding for an enzyme involved in butyrate formation; and
  wherein all the adhE genes coding for aldehyde-alcohol dehydrogenases are deleted.

20. The *Clostridium* strain of claim 18 or 19, wherein the strain is *C. acetobutylicum, C. beijerinckii, C. saccharoperbutylacetonicum, C. saccharobutylicum, C. butyricum*, or *C. cellulolyticum*.

21. A 1,3-propanediol-producing *Clostridium* strain,
  wherein the strain does not produce substantially other products of the glycerol metabolism chosen from butyrate, lactate, butanol, and ethanol;
  wherein the strain is modified to produce 1,3-propanediol by introducing at least one heterologous gene coding for an enzyme involved in the B-12 independent 1,3-propanediol pathway; and
  wherein the strain, prior to modification, can produce ethanol and the at least one heterologous gene is introduced to replace at least one gene coding for an enzyme involved in ethanol formation.

22. The *Clostridium* strain of claim 21, wherein the gene coding for an enzyme involved in ethanol formation is chosen from the adhE genes coding for aldehyde-alcohol dehydrogenases.

23. The *Clostridium* strain of claim 22, wherein all the ldh genes coding for lactate dehydrogenases are deleted.

24. The *Clostridium* strain of claim 21, wherein all the remaining adhE genes coding for aldehyde-alcohol dehydrogenases are deleted.

25. The *Clostridium* strain of claim 21, wherein the strain is *Clostridium thermocellum, Clostridium saccharolyticum* (now *Thermoanaerobacter saccharolyticum*), *Clostridium thermosulfurogenes* (now *Thermoanaerobacter thermosulfurigenes*), or *Clostridium thermohydrosulfuricum* (now *Thermoanaerobacter ethanolicus*).

26. A 1,3-propanediol-producing *Clostridium* strain,
  wherein the strain does not produce substantially other products of the glycerol metabolism chosen from butyrate, lactate, butanol, and ethanol;
  wherein the strain is modified to produce 1,3-propanediol by introducing at least one heterologous gene coding for an enzyme involved in the B-12 independent 1,3-propanediol pathway;
  wherein the microorganism is modified to decrease the hydrogen flux and to redirect the reducing power to 1,3-propanediol production; and
  wherein the hydA gene involved in hydrogen flux is attenuated.

27. A 1,3-propanediol-producing *Clostridium* strain,
  wherein the strain does not produce substantially other products of the glycerol metabolism chosen from butyrate, lactate, butanol, and ethanol;
  wherein the strain is modified to produce 1,3-propanediol by introducing at least one heterologous gene coding for an enzyme involved in the B-12 independent 1,3-propanediol pathway; and
  wherein the microorganism is modified to convert acetate to acetone.

28. The *Clostridium* strain of claim 27, wherein the genes coding for the enzymes involved in acetone formation are exogenous and are introduced into the *Clostridium* strain.

* * * * *

SEQUENCE LISTING

```
<160> NUMBER OF SEQ ID NOS: 20

<210> SEQ ID NO 1
<211> LENGTH: 36
<212> TYPE: DNA
<213> ORGANISM: Artificial Sequence
<220> FEATURE:
<223> OTHER INFORMATION: Buk 1 Primer Sequence

<400> SEQUENCE: 1
aaaaggatcc tagtaaaagg gagtgtacga ccagtg                              36

<210> SEQ ID NO 2
<211> LENGTH: 64
<212> TYPE: DNA
<213> ORGANISM: Artificial Sequence
<220> FEATURE:
<223> OTHER INFORMATION: Buk 21 Primer Sequence

<400> SEQUENCE: 2
ggggcagctg gtcgcgaaaa aagggggggat tattagtaat ctatacatgt taacattcct    60
ccac                                                                 64

<210> SEQ ID NO 3
<211> LENGTH: 53
<212> TYPE: DNA
<213> ORGANISM: Artificial Sequence
<220> FEATURE:
<223> OTHER INFORMATION: Buk 31 Primer Sequence

<400> SEQUENCE: 3 ccccctttt tcgcgaccag ctgccccact tcttgcactt gcagaaggtg gac            53

<210> SEQ ID NO 4
<211> LENGTH: 37
<212> TYPE: DNA
<213> ORGANISM: Artificial Sequence
<220> FEATURE:
<223> OTHER INFORMATION: Buk 4 Primer Sequence

<400> SEQUENCE: 4
aaaaggatcc tctaaattct gcaatatatg ccccccc                             37

<210> SEQ ID NO 5
<211> LENGTH: 28
<212> TYPE: DNA
<213> ORGANISM: Artificial Sequence
<220> FEATURE:
<223> OTHER INFORMATION: Buk 0 Primer Sequence

<400> SEQUENCE: 5
ataacaggat atatgctctc tgacgcgg                                       28

<210> SEQ ID NO 6
<211> LENGTH: 28
<212> TYPE: DNA
<213> ORGANISM: Artificial Sequence
<220> FEATURE:
<223> OTHER INFORMATION: Buk 5 Primer Sequence

<400> SEQUENCE: 6
gatcatcact cattttaaac atggggcc                                       28

<210> SEQ ID NO 7
```

```
<211> LENGTH: 39
<212> TYPE: DNA
<213> ORGANISM: Artificial Sequence
<220> FEATURE:
<223> OTHER INFORMATION: Ldh 1 Primer Sequence

<400> SEQUENCE: 7
aaaaggatcc gctttaaaat ttggaaagag gaagttgtg                      39

<210> SEQ ID NO 8
<211> LENGTH: 56
<212> TYPE: DNA
<213> ORGANISM: Artificial Sequence
<220> FEATURE:
<223> OTHER INFORMATION: Ldh 2 Primer Sequence

<400> SEQUENCE: 8
ggggaggcct aaaaggggg ttagaaatct ttaaaaattt ctctatagag cccatc    56

<210> SEQ ID NO 9
<211> LENGTH: 57
<212> TYPE: DNA
<213> ORGANISM: Artificial Sequence
<220> FEATURE:
<223> OTHER INFORMATION: Ldh 3 Primer Sequence

<400> SEQUENCE: 9 ccccctttt aggcctcccc ggtaaaagac ctaaactcca agggtggagg ctaggtc   57

<210> SEQ ID NO 10
<211> LENGTH: 48
<212> TYPE: DNA
<213> ORGANISM: Artificial Sequence
<220> FEATURE:
<223> OTHER INFORMATION: Ldh 4 Primer Sequence

<400> SEQUENCE: 10
aaaaggatcc cccattgtgg agaatattcc aaagaagaaa ataattgc            48

<210> SEQ ID NO 11
<211> LENGTH: 31
<212> TYPE: DNA
<213> ORGANISM: Artificial Sequence
<220> FEATURE:
<223> OTHER INFORMATION: Ldh 0 Primer Sequence

<400> SEQUENCE: 11
cagaaggcaa gaatgtatta agcggaaatg c                             31

<210> SEQ ID NO 12
<211> LENGTH: 31
<212> TYPE: DNA
<213> ORGANISM: Artificial Sequence
<220> FEATURE:
<223> OTHER INFORMATION: Ldh 5 Primer Sequence

<400> SEQUENCE: 12
cttcccatta tagctcttat tcacattaag c                             31

<210> SEQ ID NO 13
<211> LENGTH: 43
<212> TYPE: DNA
<213> ORGANISM: Artificial Sequence
<220> FEATURE:
<223> OTHER INFORMATION: Hyd 1 Primer Sequence

<400> SEQUENCE: 13
```

```
aaaaggatcc gcctcttctg tattatgcaa ggaaagcagc tgc            43
```

<210> SEQ ID NO 14
<211> LENGTH: 59
<212> TYPE: DNA
<213> ORGANISM: Artificial Sequence
<220> FEATURE:
<223> OTHER INFORMATION: Hyd 2 Primer Sequence

<400> SEQUENCE: 14

```
ggggaggcct aaaaggggg tatataaaat aaatgtgcct taacatctaa gttgaggcc    59
```

<210> SEQ ID NO 15
<211> LENGTH: 85
<212> TYPE: DNA
<213> ORGANISM: Artificial Sequence
<220> FEATURE:
<223> OTHER INFORMATION: Hyd 3 Primer Sequence

<400> SEQUENCE: 15

```
cccccttttt aggcctcccc gtttatcctc ccaaaatgta aaatataatt aaatatatt    60 aataaacttc gattaataaa cttcg                                          85
```

<210> SEQ ID NO 16
<211> LENGTH: 43
<212> TYPE: DNA
<213> ORGANISM: Artificial Sequence
<220> FEATURE:
<223> OTHER INFORMATION: Hyd 4 Primer Sequence

<400> SEQUENCE: 16

```
aaaaggatcc cctttagcg tataaagttt tatatagcta ttg                     43
```

<210> SEQ ID NO 17
<211> LENGTH: 33
<212> TYPE: DNA
<213> ORGANISM: Artificial Sequence
<220> FEATURE:
<223> OTHER INFORMATION: Hyd 0 Primer Sequence

<400> SEQUENCE: 17

```
catgttctat tgttactatg gaagaggtag tag                               33
```

<210> SEQ ID NO 18
<211> LENGTH: 29
<212> TYPE: DNA
<213> ORGANISM: Artificial Sequence
<220> FEATURE:
<223> OTHER INFORMATION: Hyd 5 Primer Sequence

<400> SEQUENCE: 18

```
gcagttatta taaatgctgc tactagagc                                    29
```

<210> SEQ ID NO 19
<211> LENGTH: 39
<212> TYPE: DNA
<213> ORGANISM: Artificial Sequence
<220> FEATURE:
<223> OTHER INFORMATION: THL 1 Primer Sequence

<400> SEQUENCE: 19

```
cgcggatcct ttatctgtta ccccgtatca aaatttagg                         39
```

<210> SEQ ID NO 20
<211> LENGTH: 33
<212> TYPE: DNA

```
<213> ORGANISM: Artificial Sequence
<220> FEATURE:
<223> OTHER INFORMATION: THL 2 Primer Sequence

<400> SEQUENCE: 20
gaagatcttc tagcactttt ctagcaatat tgc                                33
```